(12) United States Patent
Spangenberg et al.

(10) Patent No.: US 7,122,718 B2
(45) Date of Patent: Oct. 17, 2006

(54) MODIFICATION OF PLANT RESISTANCE TO DISEASES AND/OR PESTS

(75) Inventors: German Carlos Spangenberg, Bundoora (AU); Angela Jane Lidgett, Richmond (AU)

(73) Assignees: Dairy Australia Limited, Victoria (AU); Molecular Plant Breeding Nominees Ltd., South Australia (AU)

( * ) Notice: Subject to any disclaimer, the term of this patent is extended or adjusted under 35 U.S.C. 154(b) by 148 days.

(21) Appl. No.: 10/333,091

(22) PCT Filed: Jul. 27, 2001

(86) PCT No.: PCT/AU01/00919

§ 371 (c)(1),
(2), (4) Date: May 27, 2003

(87) PCT Pub. No.: WO02/09501

PCT Pub. Date: Feb. 7, 2002

(65) Prior Publication Data

US 2003/0196216 A1    Oct. 16, 2003

(30) Foreign Application Priority Data

Jul. 28, 2000 (AU) .................... PQ9070
Sep. 1, 2000 (AU) .................... PQ9863

(51) Int. Cl.
C12N 15/09 (2006.01)
C12N 15/29 (2006.01)
C12N 15/82 (2006.01)
A01H 5/00 (2006.01)
A01H 5/10 (2006.01)

(52) U.S. Cl. ............. 800/279; 800/278; 800/298; 800/295; 435/69.1; 435/468; 435/419

(58) Field of Classification Search .......... 800/278, 800/279, 298, 295; 435/320.1, 468, 69.1, 435/419
See application file for complete search history.

(56) References Cited

U.S. PATENT DOCUMENTS

| | | | |
|---|---|---|---|
| 5,728,570 A | 3/1998 | Matern et al. | 435/252.3 |
| 5,952,486 A | 9/1999 | Bloksberg et al. | 536/23.6 |
| 6,160,205 A | 12/2000 | Matern et al. | 800/298 |

FOREIGN PATENT DOCUMENTS

| | | |
|---|---|---|
| DE | 44 23 022 C1 | 5/1995 |
| EP | 0 516 958 A2 | 12/1992 |
| EP | 1 076 093 A1 | 2/2001 |
| WO | WO 93/05160 | 3/1993 |
| WO | WO 94/23044 | 10/1994 |
| WO | WO 00/56897 | 9/2000 |

OTHER PUBLICATIONS

Pellegrini et al. Plant Physiol. (1993) 103:509-517.*
Capellades, Montserrat, et al., "The maize caffeic acid O-methyltransferase gene promoter is active in transgenic tobacco and maize plant tissues," *Plant Molecular Biology*, 31:307-322, 1996.
Database EMBL "Lolium perenne caffeic acid O-methyltransferase (OMT2) mRNA, complete cds" XP002304215, Jan. 6, 1999.
Gauthier, Antonin et al, "Characterization of two cDNA clones which encode O-methyltransferases for the methylation of both flavonoid and phenylpropanoid compounds", *Archives of Biochemistry and Biophysics*, vol. 351, No. 2, pp. 243-249, XP002304121, Mar. 15, 1998.
McAlister, F.M. et al, "Sequence and expression of a stem-abundant caffeic acid O-methyltransferase cDNA from perennial ryegrass (*Lolium perenne*)", *Australian Journal of Plant Physiology*, vol. 25, pp. 225-235, XP002928056, 1998.

* cited by examiner

*Primary Examiner*—Medina A. Ibrahim
(74) *Attorney, Agent, or Firm*—Marina Larson & Associates, LLC

(57) ABSTRACT

The present invention relates to a method of modifying resistance of plants to diseases and/or pests by transforming the plants with a nucleic acid encoding ryegrass O-methyltransferase (OMT). The invention also relates to transformed plants, cells and seeds having increased disease and/or pest resistance by expressing rygrass O-methyltransferase (OMT).

9 Claims, 5 Drawing Sheets

Begin - 1, End - 1436

Figure 3:
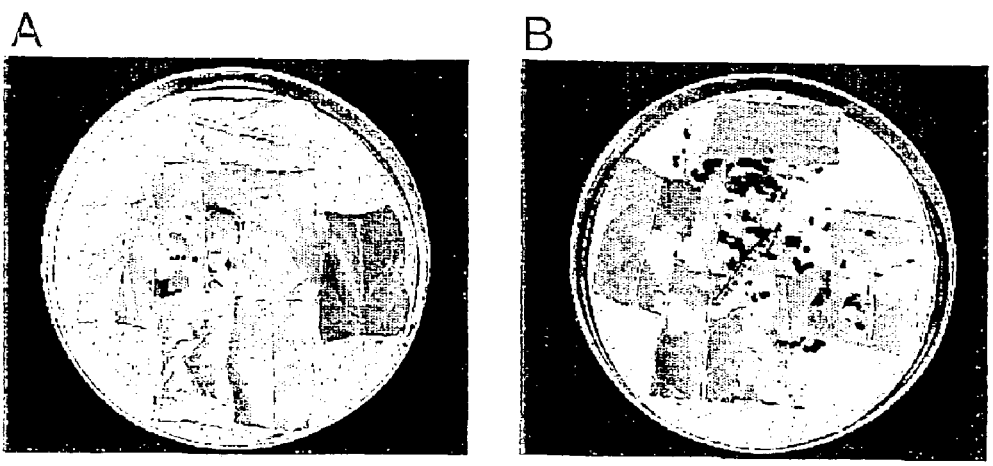

```
   1 GGCACGAGGC AAGCAGCAAC TGGTAGCATC AATCAGACCC ATCCTAGCAA
  51 GCAGCAACAG GTAGCATCAG CGACATGGCC GACGAAGAGG CGTGCATGTT
 101 CGCTCTGCAG CTGGCCAACT CGGCTGTGCT GCCGATGGCG ATTAGGACAT
 151 CCATCGAGCT GGGCCTTCTG GAGACTCTTG TGGGCGCCGG CGGGAAGTTG
 201 CTGACTCCCG AAGAGGCTGT CAAGAAGCTG CCGTCCAAGG CCAAGCACCC
 251 GGACGCGGCG TCCATGATAG ATCGCATGCT GCGTGTGCTC GCCTCGTACA
 301 AGGTGGTGAC GTGTGAGGTG GAGGAGGGCA AGGACGGCAG CCTCTCGCGC
 351 CGCTACGGCG CCACGCCGGT GTGCCGGTGG CTCGCCCCCA ACGAGGACGG
 401 CGCCTCCATG GCCCGTTCG CTCTCCTCAC CCAGGACCGC GTCTTCATGG
 451 AGGCGTGGTG CCACATGAAG GACGCGATCC TGGAGGGCGG CAGCGCGTTC
 501 CACAGGGCGT TCGGGACGTC GTGGTTCGAG TACGCAGGCC AGGACGCGCG
 551 CTTCAACCGA CTCTTCAACG AGGCCATGGA GCACCACTCG GTCATCCTCA
 601 CCAAGAAGCT CCTCGAGCTG TACAAGGGCT TCGACGGCAT CGGCACCCTG
 651 GTTGATGTGG CAGGCGGCGT GGGCGCCGTC ATCCACGCCA TCACCTCCAA
 701 GTACCCGAGC ATCAAGGGGA TCAACTTCGA CCTTCCCCAC GTCATCGCCG
 751 ACGCCCCGCC TTACCCCGGC GTGGAGCACG TCAGCGGTGA CATGTTCAAG
 801 AAGATGCCCT CCGGCGACGC CATCCTCATG AAGTGGATCC TCAACTGCTT
 851 CAGCGACGAC GAGTGCGCCA CCCTGCTCAA GAACTGCTAC GACGCGCTGC
 901 CCGCCCATGC CAAAGTCATC AACGTCGAGT GCATCTTGCC GGTGAATCCG
 951 GACGCCACCA ACGGTGCGCA GGCGTTGATC GCCGTCGATT TGAGCCTGCT
1001 TGTGTACAGC CCGGGCGGCA AGGAGAGGTA CCACAGGGAC CTGGAGAAGC
1051 TCGCCAAGGG CGCCGGCTTT ACCAGCGTCA CGGCCACCTA CATCTTCGCC
1101 GACTTCTGGG CCATGGAGTA CACTAAGTAG TAGTATCCAT GTTCCAAATT
1151 ATAAGACATT TTGGTAGTAG GCTAAAGTCA CCTACCAAAA TATCTTATAT
1201 CTACGAACGT AGGTACTACT CGACAAAGAT CATGTTATCG TGTTATATTT
1251 TCTGCTGCTT GCTATATTTC CTTCAGTTAT TATGTATTCT ACTCTTCAGA
1301 AATAAATGGC CACGCAGCGT GAGTCTGTTC ACGACGTGAG CTCAAGATGT
1351 CAACTCAGTC ATTGCATAGT CATTGCATGG ATCTTTTACT AAGCCCTAAT
1401 AAAGAGTTTG CATAAAAAAA AAAAAAAAAA AAAAAA
```

FIGURE 1

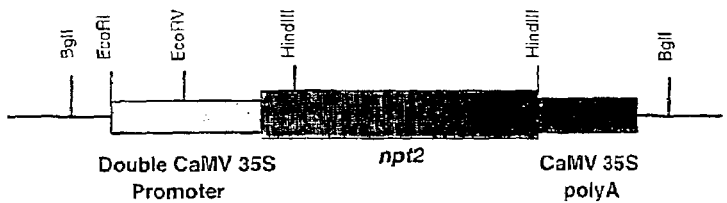
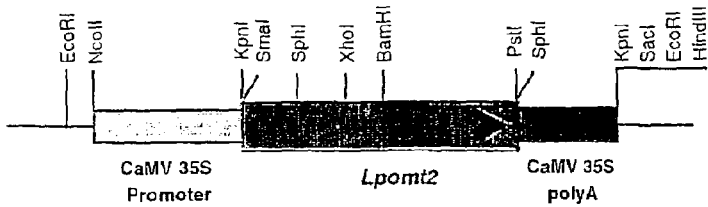
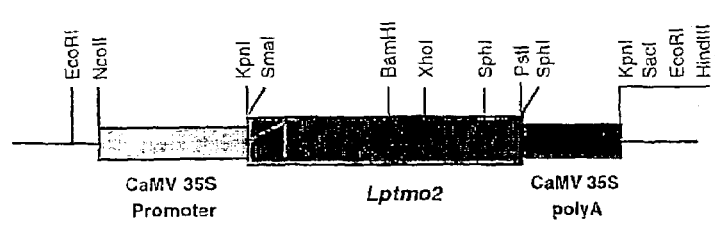
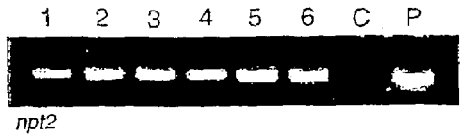
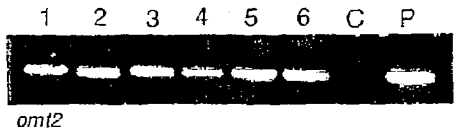
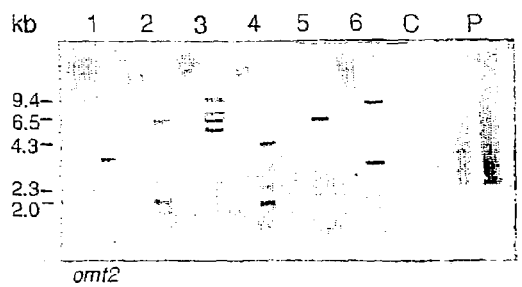
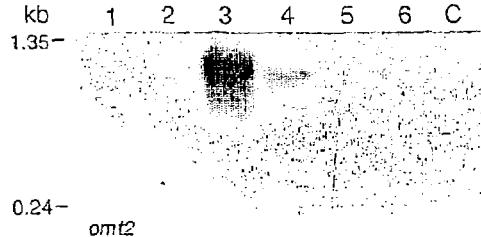
FIGURE 2

MODIFICATION OF PLANT RESISTANCE TO DISEASES AND/OR PESTS

The present invention relates to a method of modifying resistance of plants to diseases and/or pests. The invention also relates to vectors useful in such methods, transformed plants with modified resistance to diseases and/or pests, and plant cells, seeds and other parts of such plants.

Lignins are complex phenolic polymers that strengthen plant cell walls against mechanical stress and chemical degradation. Caffeic acid O-methyl transferase is a key enzyme involved in lignin biosynthesis.

Phenotypic traits which may be improved by transgenic manipulation of plants include disease and pest resistance. However, transgenic manipulation of such phenotypic traits in plants requires the availability of vectors capable of increasing resistance of plants to diseases and/or pests.

It is an object of the present invention to overcome, or at least alleviate, one or more of the difficulties or deficiencies associated with the prior art.

In one aspect, the present invention provides a method of modifying resistance to diseases and/or pests in a plant said method including introducing into said plant a nucleic acid selected from the group consisting of an O-methyltransferase homologue (OMTH) gene, a complement thereof and sequences antisense thereto; and functionally active fragments and variants thereof.

Modification of resistance to diseases and/or pests generally relates to increasing disease and/or pest resistance in the transformed plant relative to an untransformed control plant.

Disease and/or pest resistance may be increased, for example, by incorporating copies of a sense gene or a functionally active fragment or variant thereof. Disease and/or pest resistance may be also enhanced and modified, for example, by incorporating an antisense gene, or a functionally active fragment or variant thereof.

The plant should be transformed with an effective amount of said gene. By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor and Potrykus and Spangenberg, Gene Transfer to Plants, Springer Verlag, Heidelberg, the entire disclosures of which are incorporated herein by reference.

The OMTH gene may be of any suitable type. Preferably the OMTH gene is isolated from a ryegrass (*Lolium*) or fescue (*Festuca*) species. The ryegrass or fescue species may be of any suitable type, including Italian or annual ryegrass, perennial ryegrass, tall fescue, meadow fescue and red fescue. Preferably the species is a ryegrass, more preferably perennial ryegrass (*Lolium perenne*).

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

Preferably the OMTH gene is an Omt2 gene. More preferably it is an Omt2 gene from a ryegrass or fescue species, preferably a ryegrass, more preferably perennial ryegrass. Most preferably the OMTH gene has a nucleotide sequence selected from the group consisting of (a) the sequence shown in FIG. 1 hereto (SEQ ID NO: 1); (b) the complement of the sequence shown in FIG. 1 hereto; (c) sequences antisense to the sequences recited in (a) and (b); and (d) functionally active fragments and variants of the sequences recited in (a), (b) and (c).

By "functionally active" is meant that the fragment or variant (such as an analogue, derivative or mutant) is capable of modifying disease and/or pest resistance in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 10 nucleotides, more preferably at least 15 nucleotides, most preferably at least 20 nucleotides.

The disease and/or pest may be of any suitable type, and includes insects such as *Helicoverpa* species, eg. *Helicoverpa punctigera* and *Heicoverpa armigera* and fungi such as *Cercospora* species, eg. *Cercospora nicotianae*.

The gene may be introduced into said plant by any suitable technique, for example transformation. Techniques for transforming plants (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Transformed cells may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The method of the present invention may be applied to a variety of plants, including monocotyledons [such as grasses (forage and turfgrasses), corn, wheat, barley, rice and oats], dicotyledons (such as tobacco, arabidopsis, canola, cotton, clovers, alfalfa, soybean, sunflower, tomato, potato, navy beans, peas, faba beans, chickpeas, eucalyptus and maple) and gymnosperms.

In a second aspect of the present invention there is provided a vector capable of modifying resistance to diseases and/or pests in a plant, said vector including a nucleic acid selected from the group consisting of an OMTH gene, a complement thereof and sequences antisense thereto; and functionally active fragments and variants thereof.

In a preferred embodiment of this aspect of the invention, the vector may include a regulatory element such as a promoter, a nucleic acid selected from the group consisting of an OMTH gene, a complement thereof and sequences antisense thereto, and functionally active fragments and variants thereof; and a terminator; said regulatory element, nucleic acid and terminator being operatively linked.

By "operatively linked" is meant that said regulatory element is capable of causing expression of said nucleic acid in a plant cell and said terminator is capable of terminating expression of said nucleic acid in a plant cell. Preferably, said regulatory element is upstream of said nucleic acid and said terminator is downstream of said nucleic acid.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes;* phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable promoters include the Cauliflower Mosaic Virus 35S (CaMV 35S) promoter, the Cauliflower Mosaic Virus 19S (CaMV 19S) promoter, the maize Ubiquitin promoter, the rice Actin promoter, and ryegrass endogenous OMT, 4CL, CCR or CAD promoters.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes [such as beta-glucuronidase (GUS) gene (gusA), the green fluorescent protein (GFP) gene (gfp), the luciferase (LUC) gene (luc)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as polymerase chain reaction (PCR), Southern blot hybridisation analysis, histochemical GUS assays, northern and Western blot hybridisation analyses.

Those skilled in the art will appreciate that the various components of the vector are operatively linked, so as to result in expression of said nucleic acid. Techniques for operatively linking the components of the vector of the present invention are well known to those skilled in the art.

Such techniques include the use of linkers, such as synthetic linkers, for example including one or more restriction enzyme sites.

In a further aspect of the present invention there is provided a transgenic plant cell, plant, plant seed or other plant part, with modified resistance to diseases and/or pests. Preferably the transgenic plant cell, plant, plant seed or other plant part is produced by a method according to the present invention or includes a vector according to the present invention.

The present invention also provides a plant, plant seed or other plant part derived from a plant cell of the present invention.

The present invention also provides a plant, plant seed or other plant part derived from a plant of the present invention.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1 shows nucleotide sequence of the perennial ryegrass (*Lolium perenne*) OMTH plant defence gene LpOMT2 (SEQ ID NO:1).

FIG. 2 shows molecular analysis of transgenic tobacco carrying sense and antisense LpOmt2 transgenes: A) Plasmid map of transformation vector carrying a chimeric neomycin phosphotransferase npt2 gene. B–C) Plasmid maps of transformation vectors carrying a chimeric sense LpOmt2 gene [omt2] (B) or a chimeric antisense LpOmt2 gene [tmo2] (C) under control of the CaMV 35S promoter. D–E) PCR analysis of 6 independent transgenic tobacco clones using primers for the npt2 gene (D) and the omt2 gene (E). Lanes 1–4 represent tobacco clones transformed with npt2 and the sense omt2 gene vectors and lanes 5–6 represent tobacco clones transformed with npt2 and the antisense tmo2 vectors. F) Southern hybridization analysis of 6 independent transgenic tobacco plants from D) using an omt2-specific hybridization probe. G) Northern hybridization analysis of 6 independent transgenic tobacco plants from D) using an omt2-specific hybridization probe. C=untransformed negative control tobacco; P=positive control, plasmid as on B).

FIG. 3 shows functional analysis of LpOmt2 transgenically expressed in transformed tobacco (*Nicotiana tabacum*) as plant defense gene effective against the insect pest, *Helicoverpa armigera*: A) *Helicoverpa armigera* feeding on p35Somt2-transgenic tobacco leaf material. B) *H. armigera* feeding on untransformed tobacco SR1 control leaf material.

Figure 4:
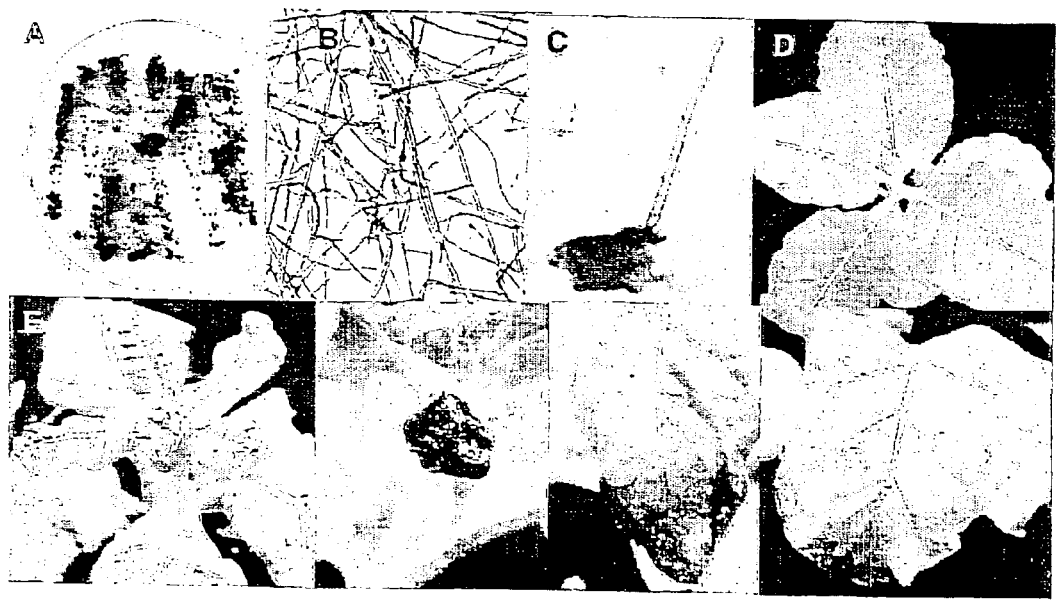

FIG. 4 shows bioassay for assessment of resistance against fungal pathogen of tobacco, *Cercospora nicotianae*: A) Sporulating culture of the tobacco fungal pathogen *Cercospora nicotianae* (sexual state). B) Hyphal filaments of *C. nicotianae* (vegetative). C) *C. nicotianae* spore. D) Non-infected untransformed tobacco leaves. E) Leaf material from untransformed tobacco infected with C. nicotianae (different stages disease and symptoms development). *Cercospora nicotianae* causes large lesions to the tobacco leaf resulting in leaf tissue death in extreme cases.

Figure 5:
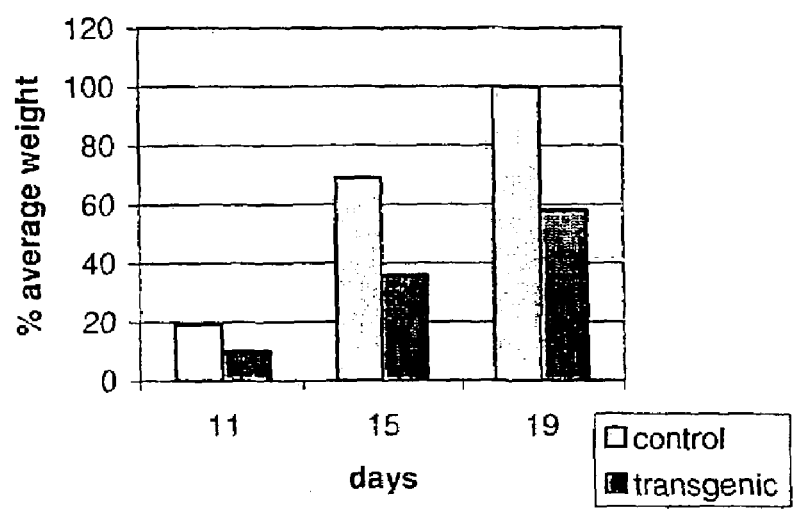

FIG. 5 shows average weight (mg) of Heliothis larvae fed on control SR1 tobacco compared to the larvae fed on LpOmt2 transgenic tobacco leaves. All weights have been expressed as a relative % of the larvae weight fed on control leaves at day 19 (maximum weight taken as 100%).

EXAMPLES

Example 1

Preparation and Molecular Analysis of Transgenic Plants

We have isolated an OMTH gene from perennial ryegrass (LpOmt2; Heath et al. J Plant Pysiol 153 pp 649 to 657 (1998); FIG. 1 hereto).

To generate plant material suitable to assess the use of the LpOmt2 gene as a plant defence gene, transgenic tobacco plants carrying a chimeric LpOmt2 gene in sense orientation under control of the CaMV 35S promoter were generated.

Sets of putative transgenic tobacco plants generated using LpOmt2 sense and antisense transformation vectors (FIG. 2BC) were initially screened by PCR and then subjected to Southern and northern hybridization analyses (FIG. 2).

A PCR screening was undertaken using npt2 and LpOmt2 specific primers for the initial identification of putative transgenic tobacco plants (FIG. 2DE). Independent transgenic tobacco plants co-transformed with both, the selectable marker npt2 gene and LpOmt2 chimeric genes, were identified.

A Southern hybridization analysis was performed with DNA samples from the PCR positive putative transgenic tobacco clones to unequivocally demonstrate their transgenic nature and the integration of the chimeric LpOmt2 transgenes. Independent transgenic tobacco plants were found to be transformed with 1 to 4 copies of the sense LpOmt2 gene omt2 (FIG. 2F, lanes 1–4), or the antisense LpOmt2 gene tmo2 (FIG. 2F, lanes 5, 6).

Northern hybridization analysis using total RNA samples prepared from the transgenic tobacco plants carrying chimeric sense or antisense LpOmt2 transgenes and the LpOmt2-specific hybridization probe revealed the presence of a 1.25 kb LpOmt2 transcript strongly expressed in 2 sense LpOmt2 transgenic tobacco plants analysed (FIG. 2G).

Example 2

Bioassays for Assessment of Resistance Against the Insect Pest, *Helicoverpa armigera*, and the Fungal Pathogen, *Cercospora nicotianae*, and Analysis of Transgenic Plants The transgenic tobacco plants found to express the LpOmt2 gene were selected for the recovery of seeds thereof and screening of germinating seeds on kanamycin to identify homo- and heterozyous transgenic plants that express the OMTH defence gene LpOmt2. The performance of these LpOmt2-expressing transgenic $T_1$ tobacco plants was measured in a bioassay with larvae of *Helicoverpa armigera* (Heliothis) (FIG. 3). Furthermore, a bioassay for assessment of transgenic plants upon infection with the test fungal pathogen of tobacco *Cerospora nicotianae* was established (FIG. 4).

The noctuid moth species *Helicoverpa armigera* and *Helicoverpa punctigera* are key pests of a variety of crops in many regions of Australia. The damage is done by the larvae, which feed on the flowering and fruiting parts of crop plants, such as cotton, sorghum, sunflower, soybeans, sweet corn, navy beans and tomatoes. Many crops are damaged by heliothis each year. Spraying is not an attractive control option as it is expensive and there is also an increasing chance that the caterpillars will become resistant to the chemical.

Heliothis larvae were fed collectively on an artificial diet for 2–3 days and then transferred to individual feeding modules containing either control tobacco leaf material or LpOmt2 transgenic tobacco leaf material. All feeding modules contained the same amount of tobacco leaf material and larvae of the same age. Feeding was monitored on a daily basis and leaf material replaced when necessary every 1–2 days. Weighing of the larvae began 7 days after the initial transfer date and then every 2 days until the onset of pupation occurred. This was observed as a decrease in body weight of the larvae. The average weight of 10 larvae fed on LpOmt2 transgenic tobacco leaves was recorded every 2 days and compared to the average weight of 10 larvae fed on control tobacco leaves.

The average weight of the larvae fed on control tobacco material increased at a greater rate than the larvae fed on the LpOmt2 transgenic material. At day 19 the average weight of the larvae fed on the control leaf material was 42% greater than that observed in larvae fed on transgenic material (FIG. 5). The onset of pupation was also delayed by 6 days in the larvae fed on the transgenic material compared to the larvae fed on the controls.

The amount of plant material consumed by the larvae and the greater size of the larvae when fed on control tobacco material compared to transgenic material can be visually observed in the photograph in FIG. 3.

These results show the use of LpOmt2 in modifying plant resistance to *Helicoverpa* species.

Documents cited in this specification are for reference purposes only and their inclusion is not an acknowledgement that they form part of the common general knowledge in the relevant art.

It will be understood that the invention disclosed and defined in this specification extends to all alternative combinations of two or more of the individual features mentioned or evident from the text or drawings. All of these different combinations constitute various alternative aspects of the invention.

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

The invention claimed is:

1. A method of increasing resistance to a disease and/or pest in a plant relative to an untransformed control plant, said method comprising introducing into said plant a nucleic acid encoding an O-methyltransferase (OMT), said nucleic acid having the nucleotide sequence of SEQ ID NO: 1.

2. The method according to claim 1, wherein said pest is an insect.

3. The method according to claim 2, wherein said insect is a *Helicoverpa* species.

4. The method according to claim 1, wherein said disease is caused by a fungus.

5. The method according to claim 4, wherein said fungus is a Cercospora species.

6. A transgenic plant with increased resistance to a disease and/or pest produced by the method according to claim 1.

7. A transgenic plant seed from the transgenic plant according to claim 6, wherein said seed has increased resistance to a disease and/or pest.

8. A transgenic plant part from the transgenic plant according to claim 6, wherein said plant part has increased resistance to a disease and/or pest.

9. A transformed plant cell, plant, seed or plant part with increased resistance to a disease and/or pest, wherein said transformed plant cell, plant, seed or plant part, each comprises a vector containing the nucleotide sequence of SEQ ID NO: 1 operably linked to a promoter.

* * * * *

UNITED STATES PATENT AND TRADEMARK OFFICE
CERTIFICATE OF CORRECTION

| | |
|---|---|
| PATENT NO. | : 7,122,718 B2 |
| APPLICATION NO. | : 10/333091 |
| DATED | : October 17, 2006 |
| INVENTOR(S) | : Spangenberg et al. |

It is certified that error appears in the above-identified patent and that said Letters Patent is hereby corrected as shown below:

In the claims:

Claim 6, Column 7 should read: --A transgenic plant cell, plant, plant seed or other part with increased resistance to a disease and/or pests produced by the method according to claim 1.--

Signed and Sealed this

Second Day of January, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 1436
<212> TYPE: DNA
<213> ORGANISM: Lolium perenne

```
<400> SEQUENCE: 1
ggcacgaggc aagcagcaac tggtagcatc aatcagaccc atcctagcaa gcagcaacag      60
gtagcatcag cgacatggcc gacgaagagg cgtgcatgtt cgctctgcag ctggccaact     120
cggctgtgct gccgatggcg attaggacat ccatcgagct gggccttctg gagactcttg     180
tgggcgccgg cgggaagttg ctgactcccg aagaggctgt caagaagctg ccgtccaagg     240
ccaagcaccc ggacgcggcg tccatgatag atcgcatgct gcgtgtgctc gcctcgtaca     300
aggtggtgac gtgtgaggtg gaggagggca aggacggcag cctctcgcgc cgctacggcg     360
ccacgccggt gtgccggtgg ctcgccccca acgaggacgc cgcctccatg gccccgttcg     420
ctctcctcac ccaggaccgc gtcttcatgg aggcgtggtg ccacatgaag gacgcgatcc     480
tggagggcgg cagcgcgttc cacagggcgt tcgggacgtc gtggttcgag tacgcaggcc     540
aggacgcgcg cttcaaccga ctcttcaacg aggccatgga gcaccactcg gtcatcctca     600
ccaagaagct cctcgagctg tacaagggct tcgacggcat cggcaccctg gttgatgtgg     660
caggcggcgt gggcgccgtc atccacgcca tcacctccaa gtacccgagc atcaagggga     720
tcaacttcga ccttccccac gtcatcgccg acgccccgcc ttaccccggc gtggagcacg     780
tcagcggtga catgttcaag aagatgccct ccggcgacgc catcctcatg aagtggatcc     840
tcaactgctt cagcgacgac gagtgcgcca ccctgctcaa gaactgctac gacgcgctgc     900
ccgcccatgc caaagtcatc aacgtcgagt gcatcttgcc ggtgaatccg gacgccacca     960
acggtgcgca ggcgttgatc gccgtcgatt tgagcctgct tgtgtacagc ccgggcggca    1020
aggagaggta ccacagggac ctggagaagc tcgccaaggg cgccggcttt accagcgtca    1080
cggccaccta catcttcgcc gacttctggg ccatggagta cactaagtag tagtatccat    1140
gttccaaatt ataagacatt ttggtagtag gctaaagtca cctaccaaaa tatcttatat    1200
ctacgaacgt aggtactact cgacaaagat catgttatcg tgtttatattt tctgctgctt    1260 gctatatttc cttcagttat tatgtattct actcttcaga aataaatggc cacgcagcgt    1320
gagtctgttc acgacgtgag ctcaagatgt caactcagtc attgcatagt cattgcatgg    1380
atcttttact aagccctaat aaagagtttg cataaaaaaa aaaaaaaaaa aaaaaa        1436
```